United States Patent [19]
Day

[11] Patent Number: 5,261,124
[45] Date of Patent: Nov. 16, 1993

[54] EYE SHIELD ASSEMBLY FOR CAP VISOR

[76] Inventor: Sheng-Tong Day, 1, Chung Yang N. Rd.,, Ching-shui, Taichung, Taiwan

[21] Appl. No.: 991,158
[22] Filed: Dec. 16, 1992
[51] Int. Cl.⁵ .................. A42B 1/20; A42B 1/24; G02C 3/02
[52] U.S. Cl. .................................. 2/10; 2/199; 2/453; 351/155
[58] Field of Search .................. 2/10, 199, 453, 12, 2/185 R; 351/155, 158

[56] References Cited

U.S. PATENT DOCUMENTS

| | | | |
|---|---|---|---|
| 2,619,641 | 12/1952 | Vaca | 2/10 |
| 2,691,164 | 10/1954 | Feldman | 2/10 |
| 2,725,560 | 12/1955 | Feldman | 2/10 |
| 4,819,274 | 4/1989 | Day | 2/10 |
| 4,951,316 | 8/1990 | Moody | 2/10 |
| 5,129,102 | 7/1992 | Solo | 2/10 |
| 5,171,152 | 12/1992 | McCleery | 2/199 X |
| 5,208,916 | 5/1993 | Kelman | 2/10 |

Primary Examiner—Peter Nerbun
Attorney, Agent, or Firm—Pro-Techtor International

[57] ABSTRACT

An eye shield assembly for cap visor, comprising a clip body consisting of a clip and a hollow frame having rails at longitudinal opposite inner sides, a slide block displaceable on the rails within the hollow frame of the clip body, which is formed with a holder portion at a bottom side, and an eye shield with a support pivotally engaged into and suspended from the holder portion of the slide block. This eye shield assembly is readily mounted onto the visor of a cap and detached as desired.

4 Claims, 3 Drawing Sheets

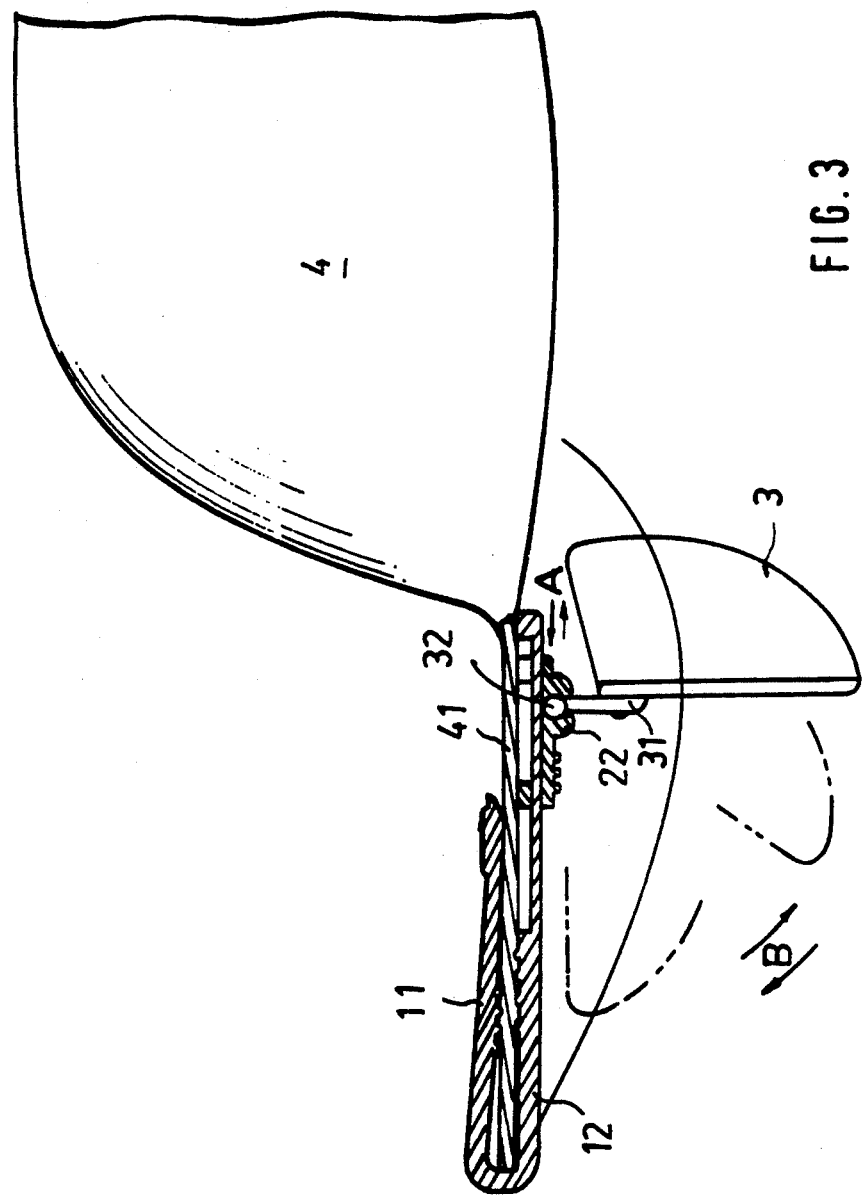

EYE SHIELD ASSEMBLY FOR CAP VISOR

BACKGROUND OF THE INVENTION

The present invention relates to an eye shield assembly for cap visor.

U.S. Pat. No. 4,819,274, issued on Apr. 11, 1989 to the same inventor of this application, discloses a visor cap with a detachable eye shield in which said visor cap comprises a mounting block that attaches the eye shield member to the visor member. With this cap visor, a dovetail groove is required to be integrally or separately formed and provided to the underside of said visor member. Without this specifically provided groove in the visor member itself, a cap commonly used cannot be attached with said mounting block and, in turn, said eye shield member.

SUMMARY OF THE INVENTION

It is, therefore, an object of the present invention to provide an eye shield assembly for cap visor, which is detachably mounted onto the visor of a cap commonly used and without the necessary to have any special groove or other attachments in said visor itself.

The aforementioned and other objects, features and advantages of the present invention will be more apparent and understood from the following description in detail, with reference to the preferred embodiments as illustrated in the accompanying drawings.

BRIEF DESCRIPTION OF THE DRAWINGS

FIG. 3 is a partly sectional view of the present eye shield assembly to illustrate that the slide block is displaceable and the eye shield is pivotable.

DETAILED DESCRIPTION OF THE PREFERRED EMBODIMENT

Figure 1:
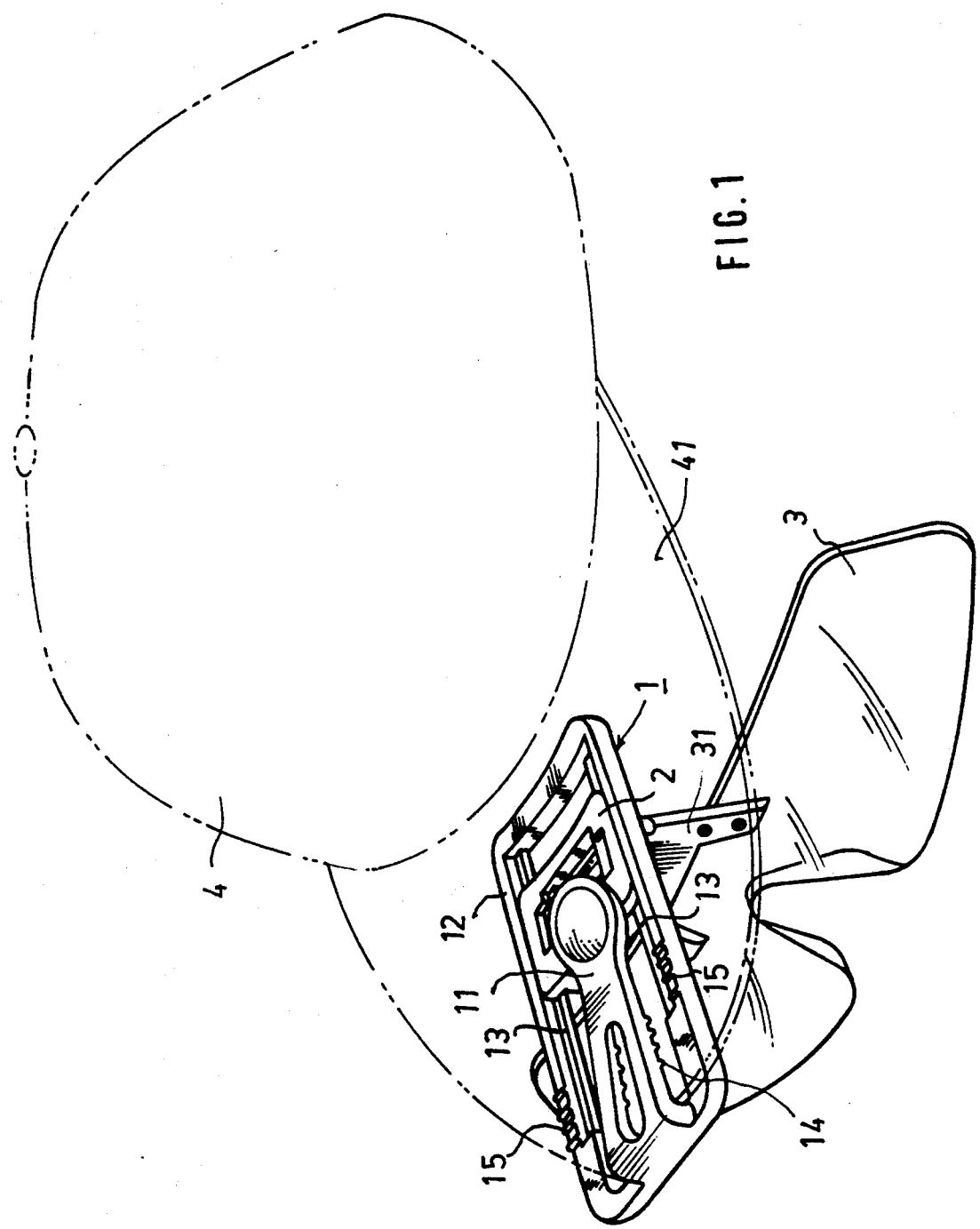
FIG. 1 is a perspective view of an eye shield assembly according to the present invention attached onto the visor of a cap.
Figure 2:
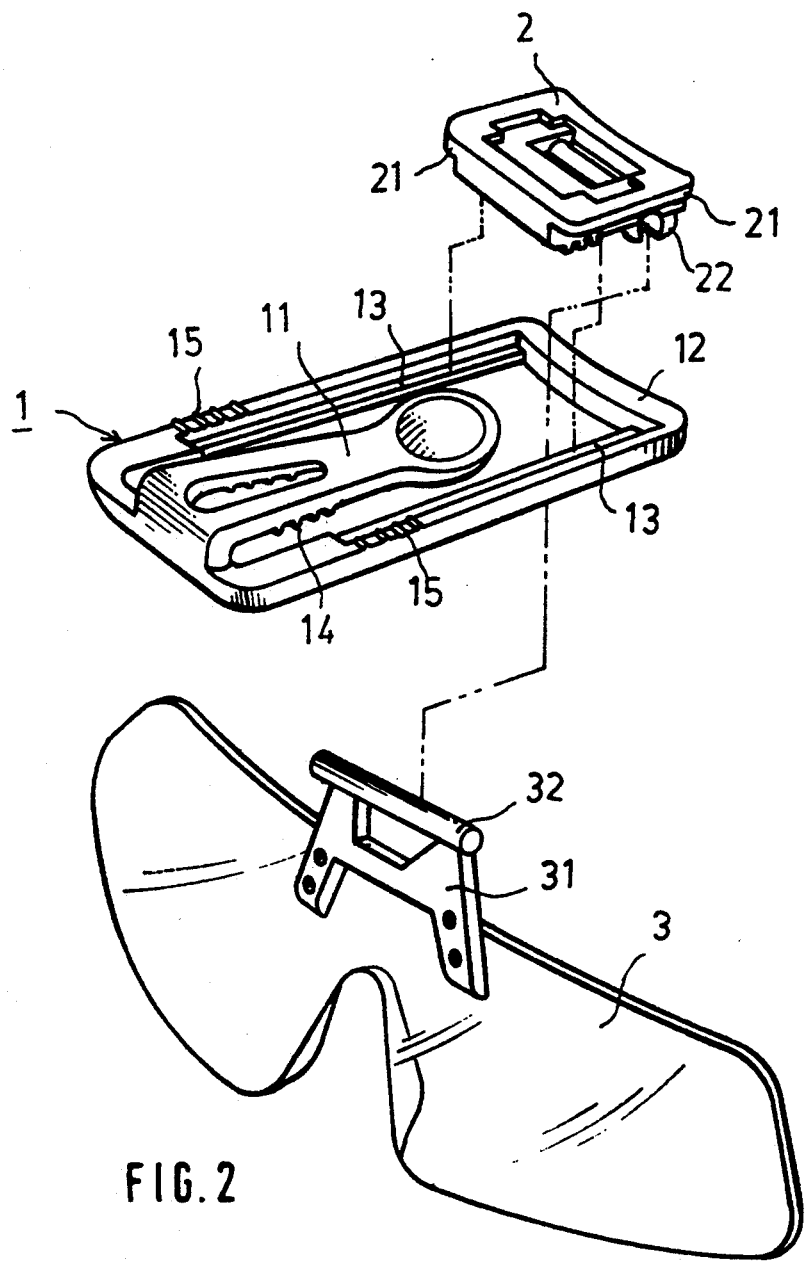
FIG. 2 is a perspective, exploded view of the present eye shield assembly.

Referring now to FIGS. 1 to 3 of the drawings, the eye shield assembly according to the present invention comprises a clip body 1, a slide block 2 and an eye shield 3.

The clip body 1 consists of a clip 11 and a hollow frame 12 integrally moulded and interconnected at, preferably, front side. At longitudinal inner sides of the hollow frame 12, there are formed with the rails 13 in the form of shoulders. The clip 11 is preferably inclined downwards at least at the free end to have a best elastic pressure against the visor 41 of a cap 4 when clipped thereon. A plurality of striations are formed in part of the underside of the clip 11 as indicated by 14 and/or the upper surface of the frame 12 as shown by 15, respectively, for enhancing the frictional engagement with said visor 41 when the clip body 1 is mounted thereon.

The slide block 2 is formed with wing portions 21 at opposite lateral sides. When said block 2 is assembled within said frame 12, the wing portions 21 are just placed over said rails 13 and slidably displaced thereon as desired along the longitudinal direction. A holder portion 22 is provided at underside of said slide block 2. The holder portion 22 is in a form of retaining groove which is preferable to have the opening a slight smaller than its inner diameter.

The eye shield 3 is suspended by a support 31 which is provided with a rod type shaft 32. Said shaft 32 is snappingly fitted into the retaining groove of the holder 22 by applying a slight force and pivotably retained therein without the risk of stripping out by accident. The length of said shaft 32 is greater than the transverse width of said frame 12, so that when the shaft 32 is fitted into said holder 22, the shaft 32 also functions as a stopper to prevent said block 2 from vibration.

As shown, the eye shield assembly is readily mounted onto the visor 41 of the cap 4 by a clipping action, in other words, by inserting the visor 41 into the present eye shield assembly in such that only the clip 11 is at upper side of said visor 41 and all other members including the frame 12 along the slide block 2 and the eye shield 3 are under said visor 41, preferably until the outmost edge of the visor 41 is stopped by the interconnection portion between said clip 11 and said frame 12. The present eye shield assembly is thus securely mounted on the visor 41 by means of the elastic clamping force of the clip 11, especially its free end, as well as the frictional engagement via the striations 14 and 15 against upper and lower surfaces of said visor 41, unless otherwise it is deliberately disengaged by applying a withdrawal force.

The block 2 is slidably displaced on the rails 13 along the longitudinal direction as indicated by the double arrow A in FIG. 3, to adjust the desirable distance of the eye shield 3 from the eyes of the user. The eye shield 3 is vertically suspended from the block 2 and also from the visor 41 at normal use as shown by the solid line in FIG. 3. But the eye shield 3 can be pivotally adjusted as indicated by the double arrow B, to any angle as schematically illustrated by the two-dot-and-dash line in FIG. 3, at the utmost till substantial parallel to the visor 41. In this state, the eye shield 3 is substantially in no use, or rather in stand-by state.

For the foregoing, it is seen that the eye shield assembly in accordance with the invention is readily mounted to the visor of any cap and replaced from a cap already used to another cap to be used instead, so that a present eye shield assembly can be used with one or more caps.

The eye shield used in this application may include sunglasses or wind shield goggles and the like.

While a preferred embodiment in accordance with the present invention has been illustrated and described, it is understood that various modifications may be resorted to without departing from the spirit and scope of the appended claims.

What is claimed is:

1. An eye shield assembly for a cap visor, comprising:
   a clip body including a clip and a hollow frame integrally molded, said hollow frame having rails extending longitudinally along its inner sides;
   a slide block formed with wing portions on each lateral side thereof, such that when said slide block is assembled within said frame, said wing portions fit onto said rails, enabling the block to slide thereon, said block further having a holder element in the form of a retaining groove at the bottom side thereof; and
   an eye shield suspended by a support which fits into the holder element and is provided with a rod which snaps into said retaining groove and is thus pivotally retained therein; and wherein the clip body is constructed so as to removably attach to the central portion of a visor of a cap, thereby enabling the assembly to be utilized on any size visor.

2. An eye shield assembly as claimed in claim 1, wherein a plurality of striations are formed in a portion of of the underside of said clip.

3. An eye shield assembly as claimed in claim 1, wherein a plurality of striations are formed in a portion of of the upper surface of said frame.

4. An eye shield assembly as claimed in claim 1, wherein said clip is preferably inclined downwards at least at a free end thereof.

* * * * *